United States Patent
Meulink

(10) Patent No.: US 8,428,693 B2
(45) Date of Patent: Apr. 23, 2013

(54) SYSTEM FOR SELECTING MODULAR IMPLANT COMPONENTS

(75) Inventor: Steven L. Meulink, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 160 days.

(21) Appl. No.: 12/758,423

(22) Filed: Apr. 12, 2010

(65) Prior Publication Data

US 2010/0198351 A1 Aug. 5, 2010

Related U.S. Application Data

(63) Continuation of application No. 11/458,257, filed on Jul. 18, 2006, now abandoned.

(51) Int. Cl.
A61B 5/00 (2006.01)

(52) U.S. Cl.
USPC .......................... 600/427; 600/411; 623/22.12

(58) Field of Classification Search ............... 623/22.12, 623/22.15; 600/407, 410, 425, 424
See application file for complete search history.

(56) References Cited

U.S. PATENT DOCUMENTS

| | | | | |
|---|---|---|---|---|
| 5,480,439 | A * | 1/1996 | Bisek et al. ................. | 128/898 |
| 5,597,384 | A | 1/1997 | Walker et al. | |
| 6,991,655 | B2 * | 1/2006 | Iversen ..................... | 623/22.12 |
| 8,202,324 | B2 | 6/2012 | Meulink et al. | |
| 2004/0138754 | A1 | 7/2004 | Lang et al. | |
| 2004/0147926 | A1 * | 7/2004 | Iversen .......................... | 606/53 |
| 2004/0171924 | A1 | 9/2004 | Mire et al. | |
| 2004/0243481 | A1 | 12/2004 | Bradbury et al. | |
| 2005/0065533 | A1 | 3/2005 | Magen et al. | |
| 2005/0085714 | A1 | 4/2005 | Foley et al. | |
| 2005/0203384 | A1 | 9/2005 | Sati et al. | |
| 2006/0065533 | A1 | 3/2006 | Inoue et al. | |
| 2007/0066917 | A1 | 3/2007 | Hodorek et al. | |
| 2007/0118243 | A1 | 5/2007 | Schroeder et al. | |
| 2007/0179626 | A1 | 8/2007 | de la Barrera et al. | |
| 2007/0233269 | A1 | 10/2007 | Steines et al. | |
| 2008/0021567 | A1 | 1/2008 | Meulink et al. | |
| 2008/0058945 | A1 | 3/2008 | Hajaj et al. | |
| 2008/0077003 | A1 | 3/2008 | Barth et al. | |
| 2012/0221114 | A1 | 8/2012 | Meulink et al. | |

OTHER PUBLICATIONS

Zimmer VerSys® Hip System—VerSys® Collared Beaded MidCoat Template Data Sheet Size 10—Size 20.
Wright Profemur® Z Total Hip System Surgical Technique Brochure.
Wright Profemur® Z/Plasma Z Total Hip System Surgical Technique Brochure.
DePuy Corail® Total Hip System Surgical Technique Brochure.

(Continued)

Primary Examiner — Unsu Jung
Assistant Examiner — Amanda Lauritzen
(74) Attorney, Agent, or Firm — Schwegman, Lundberg & Woessner, P.A.

(57) ABSTRACT

A method for selecting modular neck components for hip implants based on independent variables associated with physical characteristics of the implant, including leg length, offset, and anteversion. During surgery, the surgeon may be confronted with a need to change a preoperatively-chosen modular neck. For example, the surgeon may desire a change in at least one of the variables, e.g., leg length, offset, and/or anteversion. The present method allows the surgeon to quickly and easily select a different modular neck based on an evaluation of one of the variables without requiring reevaluation of the other variables. The method may include preoperative planning in which a template including a grid coordinate system is used.

28 Claims, 8 Drawing Sheets

OTHER PUBLICATIONS

Product Brochure—Zimmer VerSys™ Hip System Fiber Metal Taper Hip Prosthesis.

Zimmer VerSys™ Versys Fiber Metal Midcoat and Beaded Midcoat Hip Prosthesis Surgical Technique Brochure.

Profemur Z Abbreviated Surgical Technique, Wright Medical Technology, 2 pages, 2003.

Office Action mailed May 13, 2008 in parent U.S. Appl. No. 11/458,257.

Response filed Sep. 15, 2008 to the Office Action mailed May 13, 2008 in parent U.S. Appl. No. 11/458,257.

U.S. Appl. No. 11/616,369, filed Dec. 27, 2006, Modular Orthopaedic Component Case.

U.S. Appl. No. 11/458,257, filed Jul. 18, 2006, Method For Selecting Modular Implant Components.

U.S. Appl. No. 12/486,791, filed Jun. 18, 2009, Modular Orthopaedic Components.

U.S. Appl. No. 12/723,134, filed Mar. 12, 2010, Method For Selecting Modular Implant Components.

U.S. Appl. No. 13/046,849, filed Mar. 14, 2011, Modular Orthopaedic Component Case.

U.S. Appl. No. 13/465,454, filed May 7, 2012, Modular Orthopaedic Component Case.

U.S. Appl. No. 13/465,454, Non Final Office Action mailed Sep. 18, 2012, 10 pgs.

Office Action mailed Dec. 24, 2008 in parent U.S. Appl. No. 11/458,257.

Response filed Mar. 24, 2009 to the Office Action mailed Dec. 24, 2008 in parent U.S. Appl. No. 11/458,257.

Office Action mailed Apr. 2, 2009 in parent U.S. Appl. No. 11/458,257.

Response filed Jul. 2, 2009 to the Office Action mailed Apr. 2, 2009 in parent U.S. Appl. No. 11/458,257.

Office Action mailed Oct. 14, 2009 in parent U.S. Appl. No. 11/458,257.

U.S. Appl. No. 13/046,849, Final Office Action mailed Feb. 2, 2012, 9 pgs.

U.S. Appl. No. 13/046,849, Non Final Office Action mailed Jul. 25, 2011, 8 pgs.

U.S. Appl. No. 13/046,849, Notice of Allowance mailed Apr. 3, 2012, 7 pgs.

U.S. Appl. No. 13/046,849, Response filed Mar. 20, 2012 to Final Office Action, 10 pgs.

U.S. Appl. No. 13/046,849, Response filed Nov. 1, 2011 to Non Final Office Action mailed Jul. 25, 2011, 12 pgs.

\* cited by examiner

FIG_3

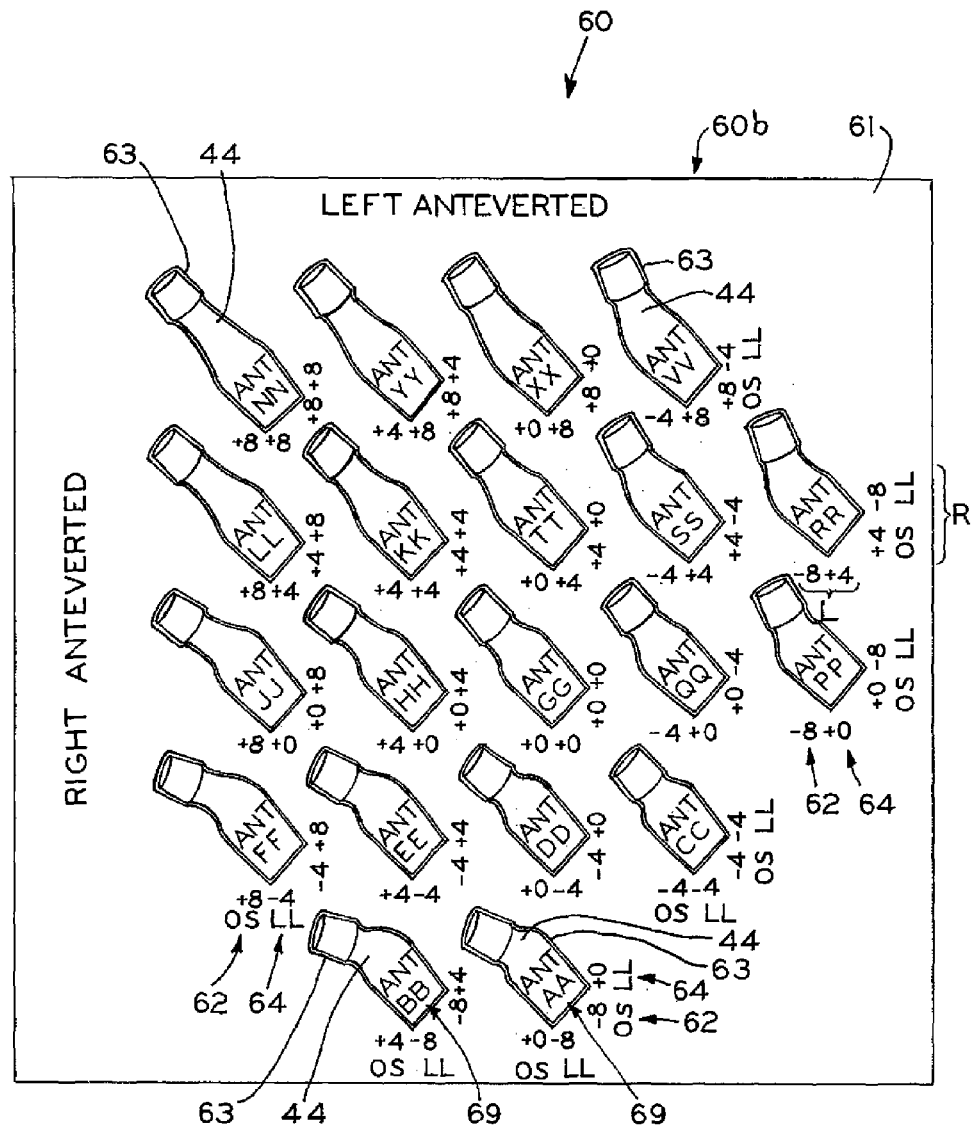
FIG_5B

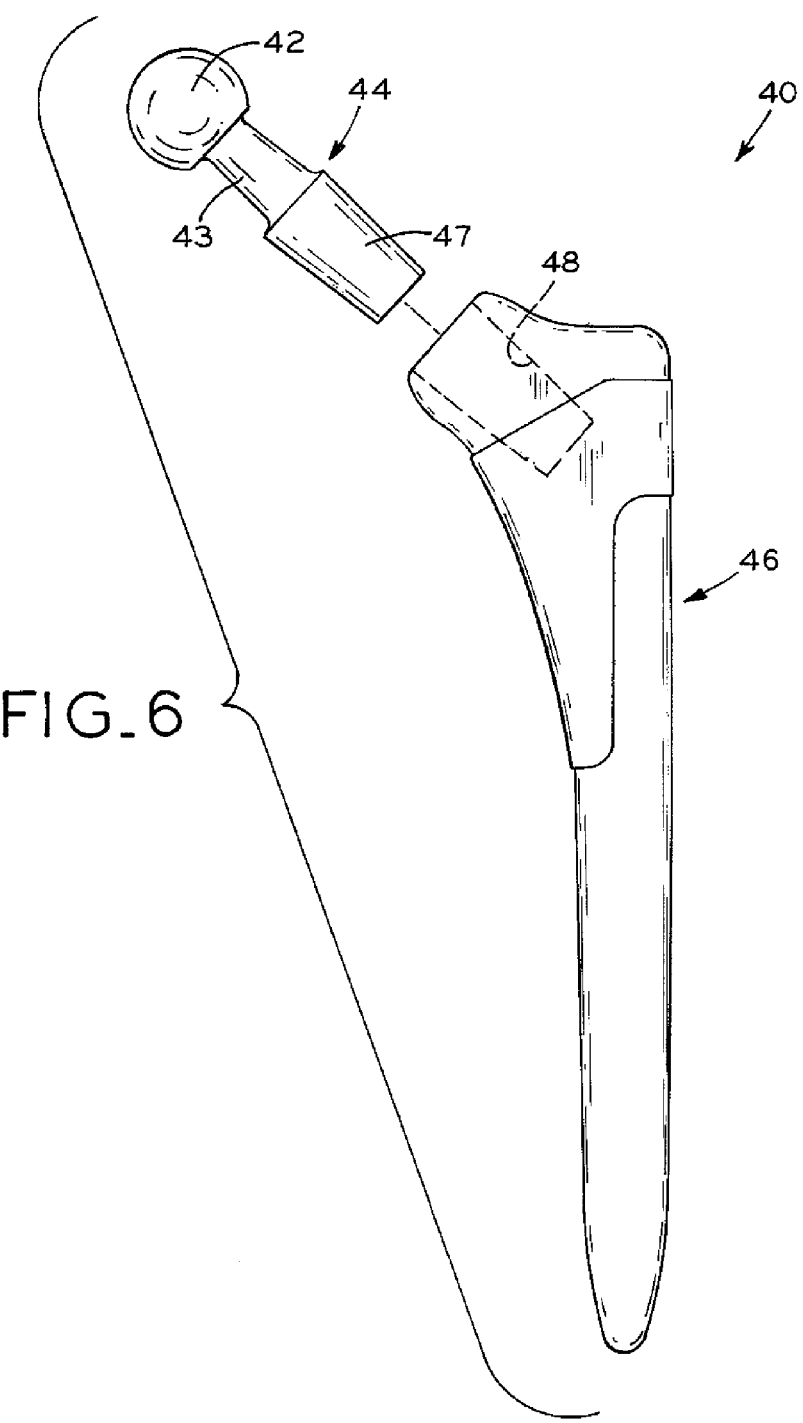

SYSTEM FOR SELECTING MODULAR IMPLANT COMPONENTS

CROSS REFERENCE TO RELATED APPLICATIONS

This application is a continuation of co-pending U.S. patent application Ser. No. 11/458,257, filed Jul. 18, 2006, entitled METHOD FOR SELECTING MODULAR IMPLANT COMPONENTS, assigned to the assignee of the present application, the disclosure of which is hereby expressly incorporated herein by reference.

BACKGROUND

1. Field of the Invention

The present invention relates to modular components for prosthetic joints. More particularly, the present invention relates to a method for selecting modular neck components for prosthetic hip joints.

2. Description of the Related Art

Orthopedic prosthetic implants are commonly used to replace some or all of a patient's hip joint in order to restore the use of the hip joint, or to increase the use of the hip joint, following deterioration due to aging or illness, or injury due to trauma. In a hip replacement, or hip arthroplasty procedure, a femoral component is used to replace a portion of the patient's femur, including the femoral neck and head. The femoral component is typically a hip stem, which includes a stem portion positioned within the prepared femoral canal of the patient's femur and secured via bone cement, or by a press-fit followed by bony ingrowth of the surrounding tissue into a porous coating of the stem portion. The hip stem also includes a neck portion adapted to receive a prosthetic femoral head. The femoral head may be received within a prosthetic acetabular component, such as an acetabular cup received within the prepared recess of the patient's acetabulum.

Orthopedic implants for hip replacement may include modular hip joint components. For example, the hip stem and the neck portion with femoral head are formed as separate components. Prior to an operation, a surgeon chooses a hip stem and a neck portion based on patient anatomy, body image scans, and/or other patient-specific data. However, during surgery, the surgeon may discover that a different hip stem or a different neck portion is desired to provide more optimum results. Modular hip joint components allow the surgeon to choose a different hip stem or neck portion depending on the specific application and needs of the patient and surgeon. Typically, the surgeon will only change the neck portion because the hip stem is usually implanted first, and removal of the hip stem from the femoral intramedullary canal is generally undesirable. Thus, the neck portion is usually the component that is most often changed intraoperatively. The surgeon may be provided with a number of different neck portions to accommodate various patient anatomies.

In one known system, for example, the surgeon chooses from a plurality of options to replace an existing neck portion with an alternative neck portion to provide the best outcome for the patient. The surgeon's choices rely on the location of the center of rotation of the femoral head component of the implant. Referring to FIG. 1, an image of a proximal femur 20 is shown and includes femoral head 22, greater trochanter 24, lesser trochanter 26, femoral neck 28, and a portion of femoral shaft 27. FIG. 1 illustrates a portion 30 of a template used in the known system. The template may also include images of the femur, similar to those described below with reference to FIGS. 3 and 4. Portion 30 of the template may be placed over the image of proximal femur 20 acquired preoperatively to plan the optimum location of the center of the femoral head of the implant. Portion 30 of the template may include a plurality of reference points 32, 34 arranged in a generally fan-shaped arrangement. Each reference point represents the center of rotation for the femoral head component of the implant. Typically, reference points 32, 34 may be based on a spherical or cylindrical coordinate system. If the surgeon desires an intra-operative change which differs from the pre-operatively chosen modular neck portion, the surgeon must simultaneously evaluate at least three variables based on the center of rotation of the femoral head of the implant, and may need to consult various tables to evaluate these variables based on physical characteristics of the patient in order to choose an optimal implant.

SUMMARY

The present invention provides a method for selecting modular neck components for hip implants based on independent variables associated with physical characteristics of the implant, including leg length, offset, and anteversion. During surgery, the surgeon may be confronted with a need to change a preoperatively-chosen modular neck. For example, the surgeon may desire a change in at least one of the variables, e.g., leg length, offset, and/or anteversion. The present method allows the surgeon to quickly and easily select a different modular neck based on an evaluation of one of the variables without requiring reevaluation of the other variables. The method may include preoperative planning in which a template including a grid coordinate system is used, which advantageously provides an intuitive system for the surgeon both preoperatively and during surgery.

In one form thereof, the present invention provides a method for selecting an orthopedic implant from a system of orthopedic implants for implantation in an anatomical structure of a patient, the method including the steps of acquiring an image of the anatomical structure; using a template with a grid coordinate system to assess at least one of a first, second, and third variable associated with respective physical characteristics of the implants, the grid coordinate system having a plurality of reference points corresponding to at least two of the first, second, and third variables; and selecting a first orthopedic implant from the system of implants based on coordinates determined using the template.

In another form thereof, the present invention provides a method for intraoperatively selecting an orthopedic implant for implantation in an anatomical structure of a patient, the method including the steps of assessing, intraoperatively, at least one of a first, a second, and a third variable associated with respective physical characteristics of the implant; and selecting an orthopedic implant based on a change in the at least one variable from a system in which the implants are arranged in subsets in which one of the others of the first, second, and third variables is constant.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 5B is a plan view of another subset of the system of modular necks used in the method illustrated in FIG. 2;

FIG. 6 is an exploded view of a modular implant.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION

The present invention generally provides a method for selecting modular neck components for hip implants based on independent variables associated with physical characteristics of the implant, including leg length, offset, and anteversion. During surgery, the surgeon may be confronted with a need to change a preoperatively-chosen modular neck. For example, the surgeon may desire a change in at least one of the variables, e.g., leg length, offset, and/or anteversion. The present method allows the surgeon to quickly and easily select a different modular neck based on an evaluation of one of the variables without requiring reevaluation of the other variables. The method may include preoperative planning in which a template including a grid coordinate system is used, which advantageously provides an intuitive system for the surgeon both preoperatively and during surgery.

Figure 1:
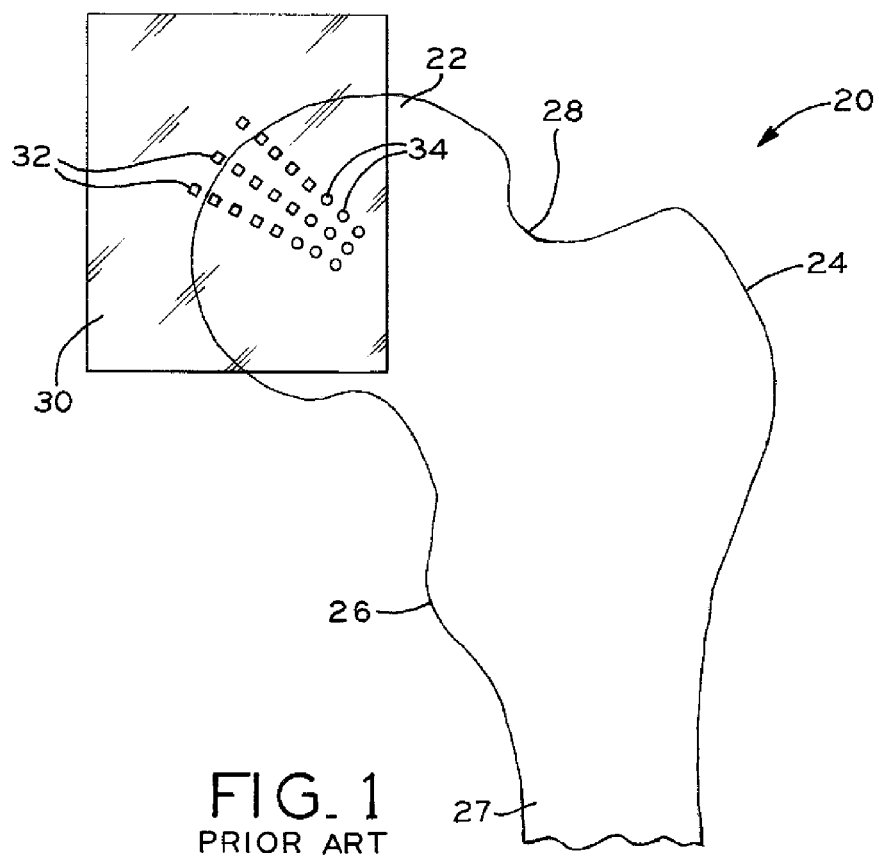
FIG. 1 is an image of a proximal femur, further showing a portion of a template of a known system overlaid on the image.
Figure 2:
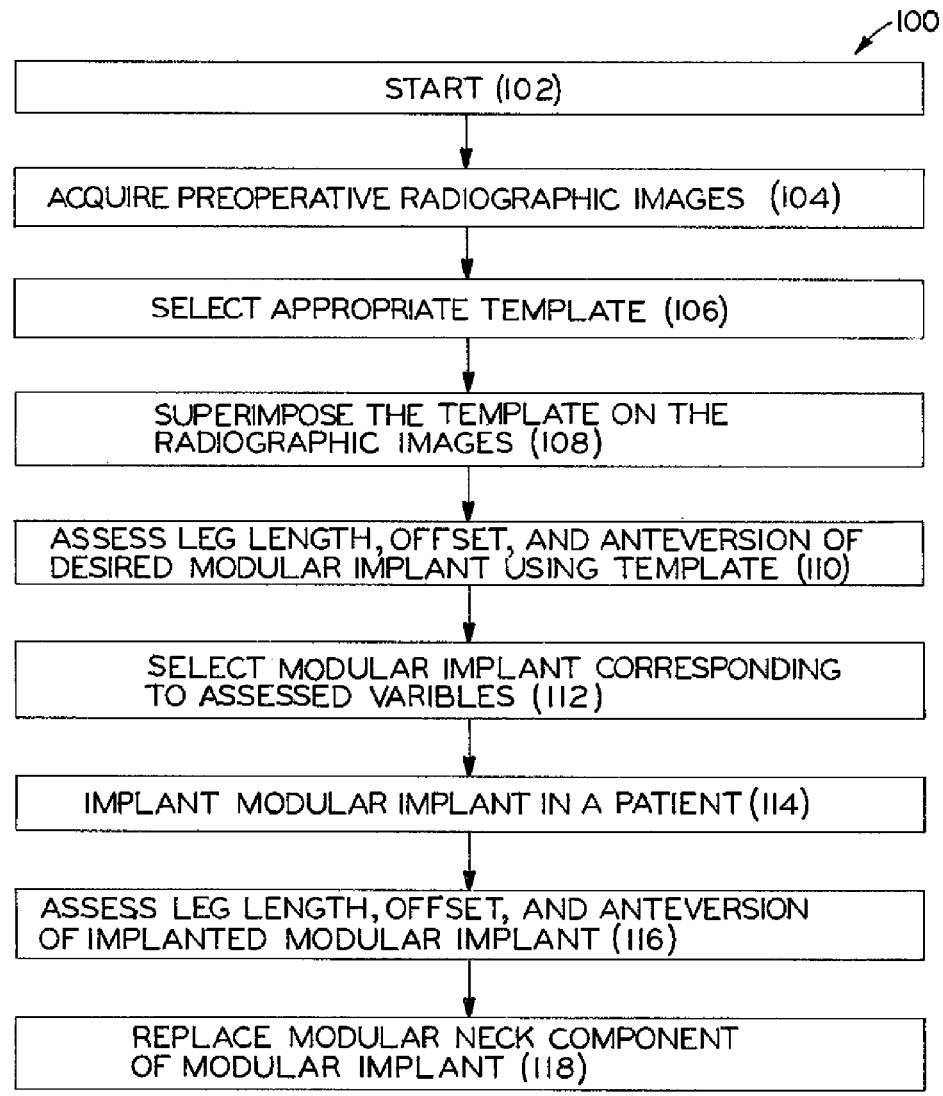
FIG. 2 is a flow chart illustrating steps of a method according to one embodiment of the present invention.

Referring to FIG. 2, a flow chart illustrating steps of method 100 is shown and includes several steps beginning with step 102. Step 102 includes preparing a patient (not shown) for the surgical procedure, e.g., collecting information and past medical history. In step 104, the surgeon or a surgeon's assistant will acquire at least one image of the appropriate portion of the hip region of the patient, e.g., at least a portion of the femur and the hip joint. The image may be a radiographic image such as an X-ray image or fluoroscopic image, for example, or, alternatively, a computed tomography (CT) image, a magnetic resonance image (MRI), or any other suitable image. Typical images for a hip replacement procedure may be taken along two different directions. For example, anterior/posterior (A/P) and lateral pelvic images may be taken of the hip joint.

Figure 3:
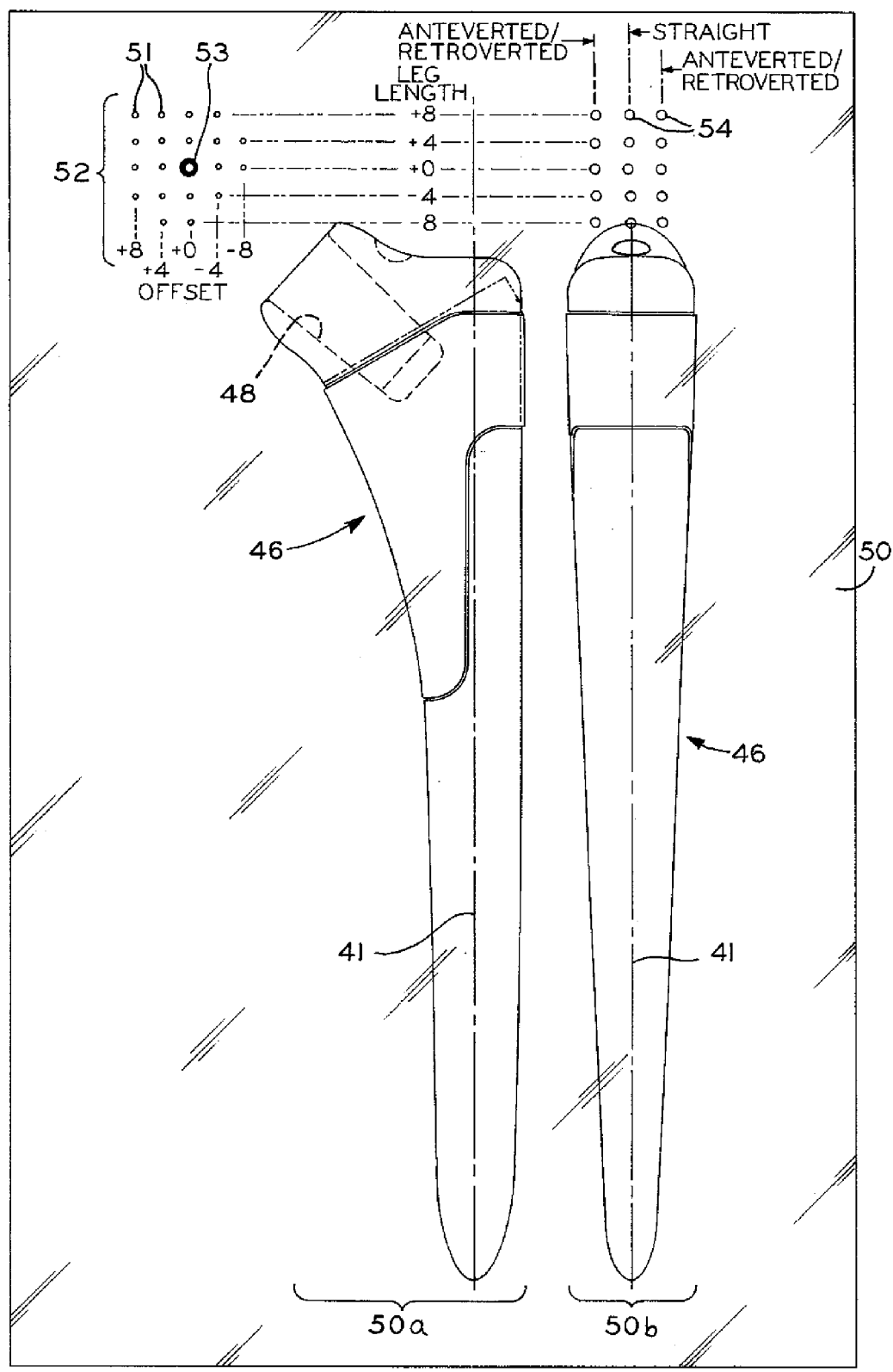
FIG. 3 is an image of a template according to one embodiment of the present invention.

Referring now to FIG. 3, a template 50 is shown which may be used in conjunction with the images to preoperatively plan a surgical procedure in order to perform the joint replacement/restoration. Template 50 may be constructed of a piece of transparent plastic or other suitable material which may be overlaid on the image of the hip portion of the patient. Template 50 may include a plurality of reference points 51 forming a grid coordinate system, for example, a Cartesian coordinate system, including a pattern of intersecting horizontal and vertical indicators or lines that provide coordinates for locating points. Reference points 51 may be formed of ink deposits on the transparent plastic, or, alternatively or in combination with the ink deposits, reference points 51 may be formed as cutouts in the transparent plastic to allow the surgeon to mark directly on the acquired image where the ideal center of rotation of the femoral head of the hip implant should be located. The grid 52 of template 50 may include leg length being measured along the "y-axis" and offset being measured along the "x-axis." Alternatively, leg length may be measured along the "x-axis" and offset may be measured along the "y-axis." Template 50 may also include graphic representations of a femoral stem component of hip implant 40 (FIG. 6), i.e., stem 46 (FIG. 6), including recess 48 shown in dashed lines in FIGS. 3 and 6. The representation of stem 46 may be formed of conventional ink on the transparent plastic. A plurality or system of templates 50 may be provided corresponding to each available size or type of femoral stem component of the hip implant system.

As shown in FIG. 3, template 50 may also include reference points 54 corresponding to the lateral pelvic view of the hip portion of the patient and which represent a third axial or cylindrical component corresponding to the anteversion component of the hip implant. Reference points 54, which are arranged in three planes, may represent an anteverted neck, a straight neck, or a retroverted neck. The planes of reference points 54 may represent the "z-axis" of grid 52 in the Cartesian coordinate system, or, alternatively, the third component may be represented in a cylindrical or polar coordinate system in which, when viewed from an end view of the proximal end of the femur, the planes in which reference points 54 are situated are arranged in a fan-shaped arrangement. More or less planes of reference points 54 may be included to accommodate a greater number of anteversion components, if needed.

In step 106, the surgeon selects the template 50 corresponding to the femoral stem component of the hip implant to be used in the surgical procedure. Template 50 may be chosen in a conventional manner such that the representation of stem 46 on template 50 substantially fills the intramedullary canal of femoral shaft 27 of the image, such that the actual femoral stem component of the hip implant will correctly fit the intramedullary canal of the actual femur.

Figure 4:
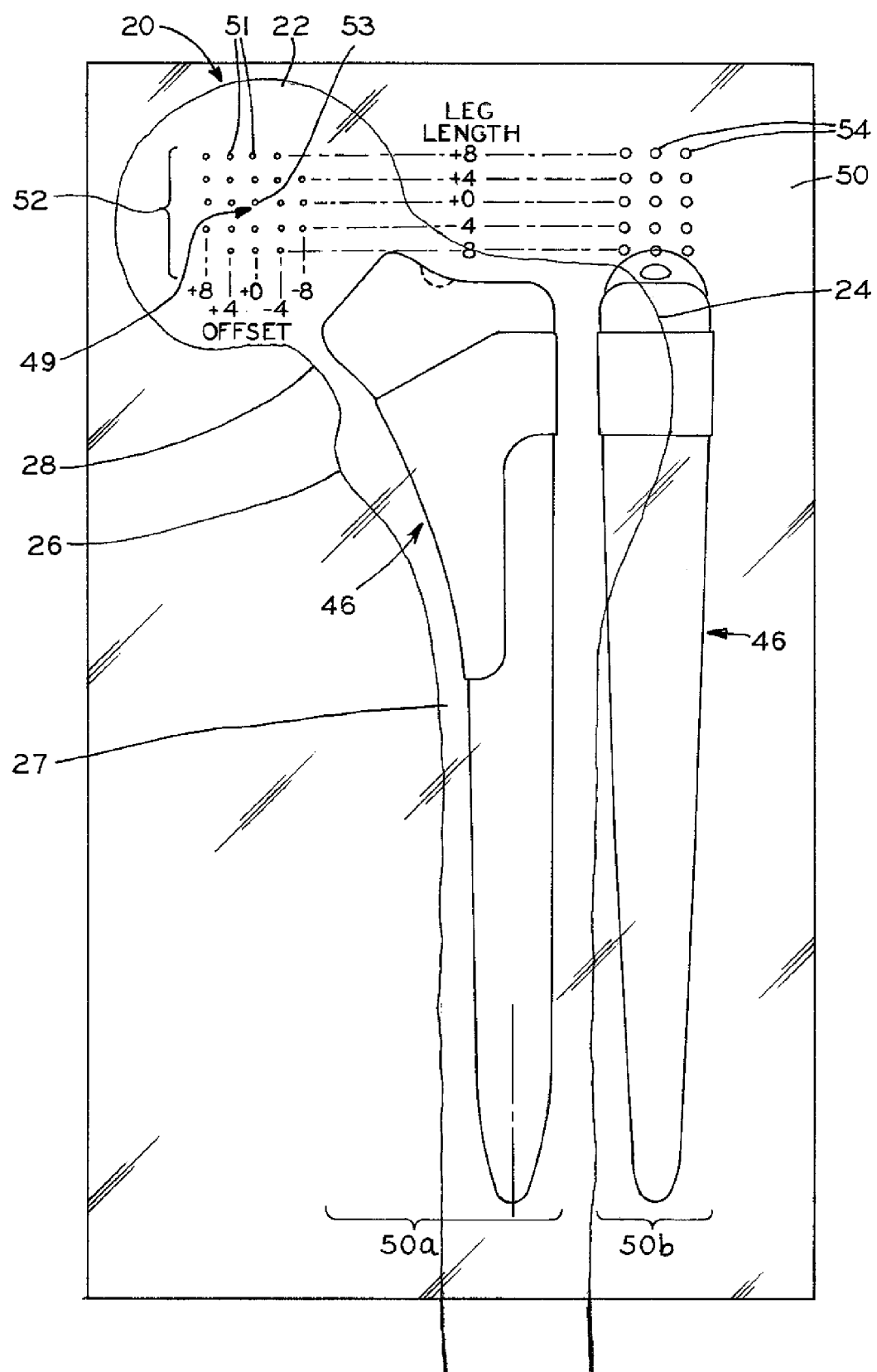
FIG. 4 is a perspective view of the template of FIG. 3 overlaid over the image of a proximal femur.

In step 108 and as shown in FIG. 4, the surgeon superimposes the correct template 50 on the acquired image. In step 110, template 50 may be used by the surgeon to determine the desired leg length and offset when using portion 50a of template 50 corresponding to the A/P pelvic view and to determine the desired anteversion and/or leg length when using portion 50b of template 50 corresponding to the lateral pelvic view. For the purposes of this document, offset is measured along a line drawn substantially perpendicular to longitudinal axis 41 of femoral stem 46. The surgeon orients the representation of stem 46 on template 50 to align with the intramedullary canal of the image of femoral shaft 27. When the surgeon is using portion 50a of template 50 corresponding to the A/P pelvic view, the surgeon orients origin 53 of grid 52 at the location at which the surgeon desires center 49 of head 42 of modular neck 44 (FIG. 6) to be located. This location of center 49 may not necessarily coincide with the original center of femoral head 22 prior to surgery because the condition of femoral head 22 may dictate a different center for the head of the modular implant component. For example, if the original femoral head 22 is severely deteriorated or is badly misshapen, the surgeon may desire a different center for the head of the modular implant than the current center for the original femoral head 22. Also, the surgeon may wish to correct some problem, e.g., laxity correction or bone alignment correction, which may cause the center for the head of the modular implant to be different than the center of femoral head 22. In an exemplary procedure, origin 53 coincides with center 49, as shown in FIG. 4. The surgeon then assesses or evaluates where center 49 should be located on grid 52 of template 50. This evaluation permits the surgeon to obtain the preoperatively-planned values for the offset and the leg length for the modular neck component of the hip implant.

Still referring to step 110 and FIG. 4, when the surgeon is using portion 50b of template 50 corresponding to the lateral pelvic view, the surgeon chooses a desired anteversion component from the planes of reference points 54. The surgeon again orients the representation of stem 46 on template 50 to align with the intramedullary canal of the image of femoral shaft 27, in the manner described above. The surgeon may use the planes of reference points 54 to determine the desired anteversion component for the modular neck of the hip implant. In an exemplary procedure, the surgeon will determine the anteversion component first, and then determine the necessary leg length and offset values for the preoperative plan of the procedure.

In step 110, the surgeon may mark directly on the image where center 49 of head 42 of modular neck 44 (FIG. 6) will be located and/or what anteversion component is necessary. In step 112, the surgeon then selects a modular neck 44 from system 60 (FIGS. 5A-5C) corresponding to the assessed variables of leg length, offset, and anteversion in the manner described below.

Alternatively, template 50 may be a template on a computer screen in a computer assisted surgery (CAS) system. The surgeon may superimpose the computer generated template 50 in the CAS system on the image of the proximal femur to determine the optimal position of center 49 of head 42 of a modular neck 44 (FIG. 6). In one such embodiment, advantageously, both views, i.e., A/P and lateral, may be simultaneously viewed in the CAS system and template 50 may be superimposed thereon to allow the surgeon to simultaneously assess all three variables, i.e., anteversion, leg length, and offset.

During surgery and as shown in step 114, a preoperatively-chosen femoral stem 46 of hip implant 40 (FIG. 6) is implanted into a patient's prepared intramedullary canal by a conventional surgical technique. The surgeon may then provisionally implant the preoperatively-chosen modular neck 44 (FIG. 6) which has been chosen by the surgeon to provide the optimum result for the particular patient, in the manner described above. Modular neck 44 (FIG. 6) may include head 42, neck portion 43, and tapered portion 47 shaped to mate with recess 48 in femoral stem 46. Head 42 may be integrally formed with neck 44 or head 42 may be a modular component attached to neck portion 43 of neck 44. Advantageously, the femoral stem 46 (FIG. 6) of hip implant 40 (FIG. 6) is equipped to accept a number of different modular neck components. Thus, the leg length, anteversion, and offset of the hip implant can be changed without requiring removal of femoral stem 46.

In step 116, the surgeon may trial the provisionally implanted modular neck 44 (FIG. 6) to verify or confirm the preoperative plan and associated results. At this point, the surgeon will assess several variables, for example, leg length, offset, and anteversion, associated with the hip implant and the physical anatomy of the patient. This assessment may be completed via a conventional surgical technique, for example, moving the joint through a range of motion. The surgeon may observe that more leg length is necessary, but that the offset and anteversion are satisfactory. The present method advantageously allows the surgeon to select a new modular neck based only on the change in leg length without affecting the offset and anteversion. Similarly, the surgeon may observe that more offset is necessary, but that the leg length and anteversion are satisfactory. The present method advantageously allows the surgeon to select a new modular neck based only on the change in offset without affecting the leg length and anteversion. Because the leg length and offset changes are based on a grid coordinate system, the surgeon can easily and intuitively select a new modular neck component based on a leg length change and/or an offset change without requiring an extensive lookup table or complicated mathematical conversion calculations to ensure that no other variables are being changed undesirably.

Similarly, the surgeon may observe that a different anteversion component is necessary, but that the leg length and offset are satisfactory. The present method advantageously allows the surgeon to select a new modular neck based only on the change in anteversion without affecting the leg length and offset. Because the anteversion component is based on a grid coordinate system, similar to leg length and offset, described above, or, alternatively, on a polar coordinate system, the surgeon can easily and intuitively select a new modular neck component based on a change in anteversion without requiring an extensive lookup table or complicated mathematical conversion calculations to ensure that no other variables are being changed undesirably.

After the surgeon determines the desired change, the surgeon may employ system 60 (FIGS. 5A-5C), described below, to choose a different modular neck 44 to provide more optimum results.

Figure 5A:
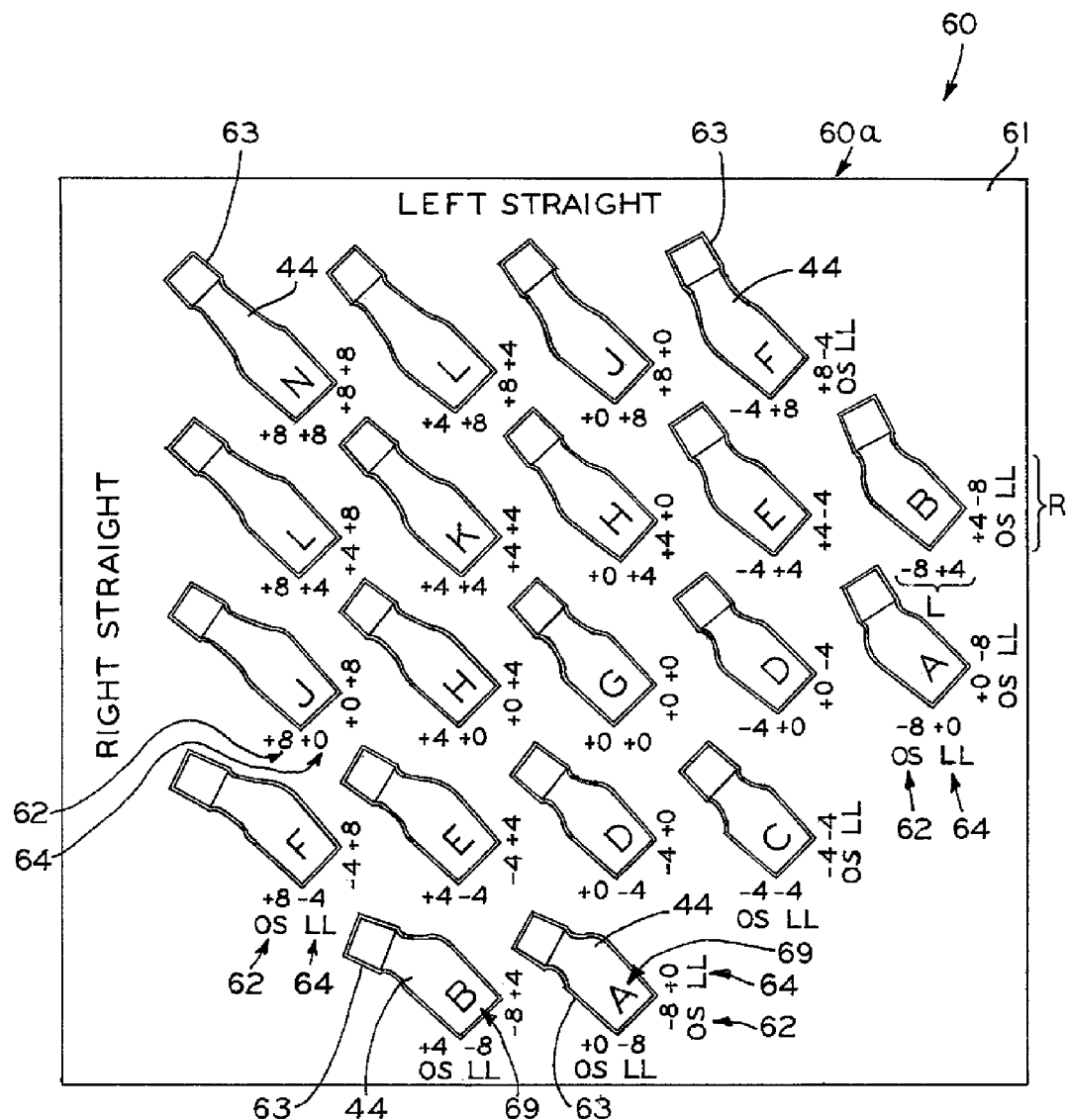
FIG. 5A is a plan view of a subset of a system of modular necks used in the method illustrated in FIG. 2.
Figure 5C:
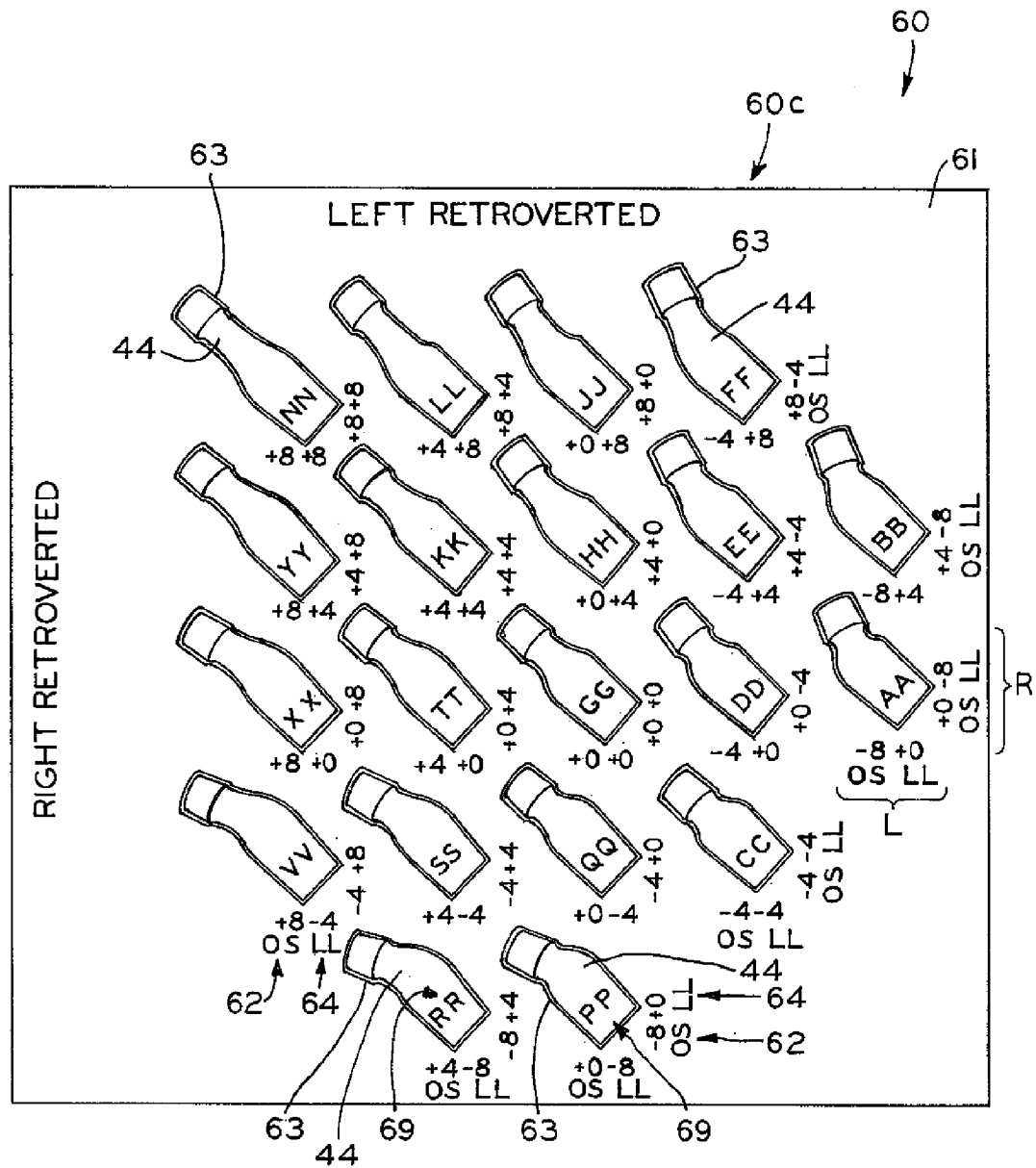
FIG. 5C is a plan view of yet another subset of the system of modular necks used in the method illustrated in FIG. 2.

Referring now to FIGS. 5A-5C, system 60 is arranged to include a plurality of modular necks 44 with varying dimensions suitable for different leg length, offset, and anteversion dimensions. In one embodiment, system 60 may include container 61 with a plurality of compartments 63 for physically housing each modular neck 44 in system 60, wherein each modular neck 44 is held in respective compartments 63 and the surgeon or an assistant selects a modular neck 44 from a compartment 63 in container 61. Each neck 44 may include reference identifier 69. In an alternative embodiment, system 60 may be a graphical representation of the plurality of modular necks 44 arranged in an organized arrangement, e.g., a Cartesian coordinate system. In this embodiment, the surgeon may select a modular neck 44 and corresponding reference identifier 69, for example, from the graphical representation, and reference identifier 69 may then be used by a surgical assistant, for example, to retrieve the desired modular neck 44 which corresponds to the surgeon's desired choice and reference identifier 69 from a central location at which the modular necks 44 are stored.

A subset of system 60 may be provided and arranged in container 61. Alternatively, a plurality of subsets of system 60 may be provided and arranged in at least one container 61. System 60 is arranged such that all necks 44 within a given subset of necks correspond to a particular anteversion component. Each subset may have a different anteversion component, thereby permitting a surgeon to independently assess the desired anteversion component and have an identical subset of necks 44 for each anteversion component. For example, the anteversion component may be, for example, anteverted, straight, or retroverted. Thus, for example, referring to FIG. 5A, subset 60a of necks 44 in system 60 may correspond to straight necks. Referring to FIG. 5B, subset 60b of necks 44 in system 60 may correspond to anteverted necks. Similarly, referring to FIG. 5C, subset 60c of necks 44 in system 60 may correspond to retroverted necks. System 60 may include as many subsets of necks 44 that correspond to the desired number of choices of the anteversion component, for example, system 60 may include additional subsets corresponding to greater extremes of anteverted and retroverted necks.

Still referring to FIGS. 5A-5C, for each neck 44 in each subset 60a, 60b, 60c of system 60, system 60 includes a pair of identifying coordinates corresponding to leg length and offset. For example, the number represented by offset component 62 corresponds to offset and the number represented by leg length component 64 corresponds to leg length. The Cartesian coordinates represented by offset component 62 and leg length component 64 may be represented by the following coordinates: (±offset, ±leg length). If origin 53 does coincide with center 49 during the preoperative planning, then the surgeon may likely choose a modular neck 44 with the following coordinates in step 112: (+0, +0). If origin 53 does not coincide with center 49 during the preoperative planning due to, for example, a defect in femoral head 22, then the surgeon may choose a modular neck with coordinates different from (+0, +0) in step 112.

Each subset 60a, 60b, 60c may include two sets of pairs of identifying coordinates corresponding to leg length and offset. Each set corresponds to either a right hip or a left hip. Advantageously, as shown in FIGS. 5A-5C, the surgeon need only rotate container 61 ninety degrees to switch between a system used for the left hip and the right hip. For example, as shown in FIG. 5A, the left hip pair of coordinates is identified by the letter L and the right hip pair of coordinates is identified by the letter R. Furthermore, as identified at the top of container 61, the anteversion component includes a designation "right" or "left" depending on which hip those necks 44 are to be used for. For example, if the surgeon needs a straight neck for a left hip, then the surgeon rotates container 61 including subset 60a until "LEFT STRAIGHT" appears at the top of container 61, as shown in FIG. 5A, at which point the offset and leg length coordinates are positioned below each respective neck 44. Alternatively, the offset and leg length coordinates may be positioned above each respective neck 44.

Intraoperatively, if the surgeon does not want any change in offset but needs a change in leg length, the surgeon will choose a new neck 44 having the following coordinates: (preoperatively-planned offset value, preoperatively-planned leg length value±change in leg length) from a particular subset according to the chosen anteversion component. Similarly, if the surgeon does not want any change in leg length but needs a change in offset, the surgeon will choose a neck 44 having the following coordinates: (preoperatively-planned offset value±change in offset, preoperatively-planned leg length value) from a particular subset according to the chosen anteversion component.

Advantageously, arranging the plurality of modular necks 44 in each subset 60a, 60b, 60c of system 60 in a Cartesian coordinate grid allows the surgeon to easily and intuitively intraoperatively choose a modular neck 44 which corresponds to an independent change in leg length, offset, or anteversion. The surgeon may use a fluoroscopic or other image-guided system (not shown) to facilitate the assessment of the change in leg length, offset, and/or anteversion, as described above, or, alternatively, the surgeon may simply manually/visually determine the desired change in leg length, offset, and/or anteversion, and subsequently choose a neck 44 from a subset of system 60 corresponding to the desired change.

In one example, if the surgeon determines in step 116 that more or less leg length is desired but that the offset and anteversion are satisfactory, the surgeon may select a different modular neck 44 from a subset of system 60 which corresponds to the desired change. For example, if the surgeon needs no change in offset and 4 millimeters (mm) more of leg length, the surgeon chooses the neck with the following coordinates from a subset of system 60 corresponding to the satisfactory anteversion component: (preoperatively planned offset value, preoperatively-planned leg length value plus 4). Subsequently, the surgeon implants neck 44 into the femoral stem component of the hip implant. The surgeon may similarly choose a different neck 44 depending on how much change in leg length was desired.

In another example, if the surgeon determines in step 116 that less leg length and more offset are desired but the anteversion is satisfactory, the surgeon may select a different modular neck 44 from a subset of system 60 which corresponds to the desired change. For example, if the surgeon needs 4 mm more of offset and 4 mm less of leg length, the surgeon chooses the neck with the following coordinates from a subset of system 60 corresponding to the satisfactory anteversion component: (preoperatively-planned offset value plus 4, preoperatively-planned leg length value minus 4). Subsequently, the surgeon implants neck 44 into the femoral stem component of the hip implant. The surgeon may similarly choose a different neck 44 depending on how much change in leg length and/or offset was desired.

In yet another example, if the surgeon determines in step 116 that leg length and offset are satisfactory but the anteversion needs changed, the surgeon may select a different modular neck 44 from a subset of system 60 which corresponds to the desired change. For example, if the surgeon needs to change from a retroverted neck to a straight neck, the surgeon will select neck 44 from subset 60a of system 60 corresponding to a straight neck and having the desired leg length and offset.

In step 118, the different neck 44 chosen by the assessment of leg length, offset, and anteversion in step 116 is implanted into the stem component of the hip implant.

Although illustrated throughout as having intervals of 4 mm for both offset and leg length, system 60 could be arranged to have intervals of any dimension to accommodate the needs of a particular patient or the desires of a particular surgeon. For example, the interval could be 1, 2, 3, 4, or 5 mm, or any fraction thereof, for both offset and leg length.

The above-described concept has generally been described as a system having three variables, i.e., leg length, offset, and anteversion. The system has been described in which one of these three variables, i.e., the anteversion component, is constant for any given subset of implants having various offsets and leg lengths. For example, the surgeon may pre-operatively choose a desired anteversion component, which may not change intraoperatively, and then need only choose various modular necks 44 from the subset corresponding to the desired anteversion component of system 60 based only on offset and leg length. Alternatively, the system may be constructed such that leg length is the constant variable and the implants of each subset of system 60 are arranged to have identical leg lengths and varying offset and anteversion components. In another alternative embodiment, the system may be constructed such that offset is the constant variable and the implants of each subset of system 60 are arranged to have identical offsets and varying leg lengths and anteversion components.

Although described throughout with respect to a hip implant, the method could be utilized in any procedure which uses modular components, for example, but not limited to, shoulder implant procedures, knee implant procedures, etc.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A system for facilitating selection of an orthopedic implant for implantation in an anatomical structure of a patient using an image of the anatomical structure, the system comprising:
    a template comprising a reference marker and a grid coordinate system including a plurality of reference points, the reference marker configured to locate the template and the plurality of reference points relative to the image of the anatomical structure; and
    a plurality of orthopedic implants, each of the plurality of orthopedic implants referenced to one of the plurality of reference points of the template,
    wherein the grid coordinate system corresponds to at least a first variable, a second variable and a third variable, the first variable being associated with a length characteristic of the plurality of orthopedic implants, the second variable being associated with an offset characteristic of the plurality of orthopedic implants, and the third variable being associated with an anteversion characteristic of the plurality of orthopedic implants, with the first variable being arranged along a first axis of the grid coordinate system, the second variable being arranged along a second axis of the grid coordinate system which is orthogonal to the first axis, and the third variable being arranged along a third axis of the grid coordinate system which is orthogonal to the first and second axes.

2. The system of claim 1, wherein the template is configured to overlay the image of the anatomical structure.

3. The system of claim 1, wherein the template is transparent.

4. The system of claim 1, wherein the plurality of orthopedic implants comprises a plurality of modular neck components for an orthopedic hip implant.

5. The system of claim 4, wherein the reference marker represents an orthopedic stem configured to couple to the modular neck components.

6. The system of claim 1, wherein said plurality of orthopedic implants includes at least one subset in which at least one of said first, second, and third variables is constant and at least another of the first, second, and third variables varies.

7. The system of claim 1, wherein the reference marker represents a first orthopedic stem.

8. The system of claim 7, further comprising a second template that includes a second reference marker, the second reference marker representing a second orthopedic stem that differs in size from the first orthopedic stem.

9. The system of claim 1, wherein the plurality of orthopedic implants includes a first implant and a second implant, at least one of the length characteristic, the offset characteristic, and the anteversion characteristic of the first implant differing from the respective characteristic of the second implant.

10. The system of claim 1, wherein the plurality of orthopedic implants comprises an arrangement of implants including at least one subset in which at least one of the first, second, and third variables is constant and the others of the first, second, and third variables varies.

11. The system of claim 10, wherein the arrangement comprises a graphical representation arranged according to the at least one subset.

12. The system of claim 1, further comprising a plurality of orthopedic implant identifiers, wherein each of the orthopedic implant identifiers is associated with one of the plurality of reference points such that moving from a first reference point to a second reference point on the grid coordinate system identifies, respectively, a corresponding change from a first orthopedic implant to a second orthopedic implant for implantation in the anatomical structure of the patient.

13. The system of claim 12, wherein the plurality of orthopedic implants are modular components of a hip implant system.

14. The system of claim 12, wherein said plurality of orthopedic implants includes at least one subset in which at least one of the first, second, and third variable is constant and at least another of the first, second, and third variables varies.

15. The system of claim 12, wherein the orthopedic implant identifiers are part of a graphical representation of the grid coordinate system.

16. The system of claim 12, wherein the orthopedic implant identifiers are incorporated onto the orthopedic implants.

17. A system for facilitating selection of an orthopedic implant for implantation in an anatomical structure of a patient using an image of the anatomical structure, the system comprising:
    a template comprising a reference marker and a grid coordinate system that identifies a plurality of alternative reference points within the template, the reference marker configured to locate the template and the plurality of alternative reference points relative to the image of the anatomical structure; and
    a plurality of modular neck components for an orthopedic hip implant, each of the plurality of modular neck components corresponding to one of the plurality of alternative reference points,
    wherein the grid coordinate system corresponds to first, second, and third implant variables associated with respective different physical characteristics of the modular neck components, the first implant variable corresponding to leg length, the second implant variable corresponding to offset, and the third implant variable corresponding to anteversion,
    wherein the first variable is arranged along a first axis of the grid coordinate system, the second variable is arranged along a second axis of the grid coordinate system which is orthogonal to the first axis, and the third variable is arranged along a third axis of the grid coordinate system which is orthogonal to the first and second axes.

18. The system of claim 17, wherein the template is configured to overlay the image of the anatomical structure.

19. The system of claim 17, wherein said plurality of orthopedic implants includes at least one subset in which at least one of said first, second, and third implant variables is constant and at least another of the first, second, and third implant variables varies.

20. The system of claim 17, wherein the reference marker represents a first orthopedic stem.

21. The system of claim 20, further comprising a second template that includes a second reference marker, the second reference marker representing a second orthopedic stem that differs in size from the first orthopedic stem.

22. The system of claim 17, wherein the plurality of orthopedic implants includes a first implant and a second implant, at least one of the length characteristic, the offset characteristic, and the anteversion characteristic of the first implant differing from the respective characteristic of the second implant.

23. The system of claim 17, wherein the plurality of orthopedic implants comprises an arrangement of implants including at least one subset in which at least one of the first, second, and third implant variables is constant and the others of the first, second, and third implant variables varies.

24. The system of claim 23, wherein the arrangement comprises a graphical representation arranged according to the at least one subset.

25. The system of claim 17, further comprising a plurality of orthopedic implant identifiers, wherein each of the orthopedic implant identifiers is associated with one of the plurality of alternative reference points such that moving from a first reference point to a second reference point on the grid coordinate system identifies, respectively, a corresponding change from a first orthopedic implant to a second orthopedic implant for implantation in the anatomical structure of the patient.

26. The system of claim 25, wherein the orthopedic implant identifiers are part of a graphical representation of the grid coordinate system.

27. The system of claim 25, wherein the orthopedic implant identifiers are incorporated onto the orthopedic implants.

28. A system for facilitating selection of an orthopedic implant for implantation in an anatomical structure of a patient using an image of the anatomical structure, the system comprising:
- a template comprising a reference marker and a grid coordinate system including a plurality of reference points, the reference marker configured to locate the template and the plurality of reference points relative to the image of the anatomical structure;
- a plurality of orthopedic implants, each of the plurality of orthopedic implants referenced to one of the plurality of reference points of the template; and
- a plurality of orthopedic implant identifiers, wherein each of the orthopedic implant identifiers is associated with one of the plurality of reference points such that moving from a first reference point to a second reference point on the grid coordinate system identifies, respectively, a corresponding change from a first orthopedic implant to a second orthopedic implant for implantation in the anatomical structure of the patient, wherein the orthopedic implant identifiers are part of a graphical representation of the grid coordinate system.

\* \* \* \* \*